US010307500B2

(12) United States Patent
Kellett

(10) Patent No.: US 10,307,500 B2

(45) Date of Patent: Jun. 4, 2019

(54) METHOD FOR NEUTRALIZING BIOLOGICAL ORGANISMS

(71) Applicant: Ensign-Bickford Aerospace & Defense Company, Simsbury, CT (US)

(72) Inventor: Richard M. Kellett, Palmer, MA (US)

(73) Assignee: ENSIGN-BICKFORD AEROSPACE & DEFENSE COMPANY, Simsbury, CT (US)

( * ) Notice: Subject to any disclaimer, the term of this patent is extended or adjusted under 35 U.S.C. 154(b) by 0 days.

(21) Appl. No.: 15/877,962

(22) Filed: Jan. 23, 2018

(65) Prior Publication Data

US 2018/0243457 A1 Aug. 30, 2018

Related U.S. Application Data

(62) Division of application No. 15/241,122, filed on Aug. 19, 2016, now Pat. No. 9,907,873.

(60) Provisional application No. 62/208,957, filed on Aug. 24, 2015, provisional application No. 62/207,950, filed on Aug. 21, 2015.

(51) Int. Cl.

*F42B 12/50* (2006.01)
*A61L 2/20* (2006.01)
*A61L 2/26* (2006.01)
*A61L 2/06* (2006.01)

(52) U.S. Cl.

CPC ................ *A61L 2/204* (2013.01); *A61L 2/06* (2013.01); *A61L 2/26* (2013.01); *F42B 12/50* (2013.01); *A61L 2202/16* (2013.01)

(58) Field of Classification Search

CPC ................................ F42B 12/50; A61L 2/204
USPC ................................................. 588/406, 313
See application file for complete search history.

(56) References Cited

U.S. PATENT DOCUMENTS

| | | | |
|---|---|---|---|
| 5,422,068 | A | 6/1995 | Shalaby et al. |
| 2017/0049917 | A1 | 2/2017 | Kellett |

*Primary Examiner* — Edward M Johnson
(74) *Attorney, Agent, or Firm* — Cantor Colburn LLP

(57) ABSTRACT

A system and method for neutralizing a biological organism is provided. The system includes a first element is made from paraformaldehyde. A second element is configured to generate heat and decompose the paraformaldehyde into formaldehyde gas. In one embodiment, the second element is configured to have an exothermic and self-sustaining alloying reaction in response to being thermally energized by an initiator.

7 Claims, 3 Drawing Sheets

METHOD FOR NEUTRALIZING BIOLOGICAL ORGANISMS

CROSS-REFERENCE TO RELATED APPLICATIONS

This application is a Divisional Application of U.S. Non-Provisional application Ser. No. 15/241,122 filed Aug. 19, 2016, which claims benefit of U.S. Provisional Application 62/207,950 filed Aug. 21, 2015 and U.S. Provisional Application 62/208,957 filed Aug. 24, 2015, the contents of all of which are incorporated by reference in their entirety.

BACKGROUND

The subject matter disclosed herein relates to a system for delivering a material that neutralizes and biological organisms, and in particular to an aerial delivery device that gasifies a material to neutralize biological threats and decontaminate an environment.

Biological threats or agents are organisms that may cause harm or sickness to humans or other mammals. Some of these organisms, such as *Bacillis anthracis* (i.e. anthrax) have been modified such that they may delivered in a concentrated form in an attempt to cause harm. When such an organism is released, the area in which the release takes place becomes unsuitable for habitation. Cleaning or decontamination is difficult because these organisms, some of which are bacterial endospores, are resistant to treatments such as heat, desiccation, radiation, pressure and chemicals. Some fumigants, such as chloride dioxide, hydrogen peroxide, formaldehyde and ethylene oxide, have been successfully used in decontaminating large rooms or buildings.

To perform the decontamination, gas generators need to be delivered into the contaminated area. As a result, human operators also need to enter the area to set up and initiate the operation of the gas generators. It should be appreciated that the human operators need to wear protective clothing and equipment (e.g. face shields and respirators) to avoid contact with the biological threat. When the contaminated area is located in a battlefield or another area that is not readily accessible, the delivery of the gas generator may not be possible.

Accordingly, while existing systems and methods of decontaminating an environment of biological threats are suitable for their intended purposes the need for improvement remains, particularly in providing a system that contains the decontamination material in a stable state and can selectively transform the decontamination material into a gaseous form to neutralize the biological threat.

BRIEF DESCRIPTION

According to one aspect of the disclosure a system for neutralizing a biological organism is provided. The system includes a first element made from paraformaldehyde. A second element is configured to generate heat and decompose the paraformaldehyde into formaldehyde gas. In one embodiment, the second element is configured to have an exothermic and self-sustaining alloying reaction in response to being thermally energized by an initiator.

According to another aspect of the disclosure a method of decontaminating an area having biological organisms. The method includes the steps of delivering a decontamination device to the area, the decontamination device having an igniter, a first element made from paraformaldehyde, and a second element; thermally energizing the second element with the igniter; forming an exothermic reaction in the second element in response to being thermally energized by the igniter; transforming the paraformaldehyde into gaseous formaldehyde with the exothermic alloying reaction; and neutralizing the biological organisms with the gaseous formaldehyde.

These and other advantages and features will become more apparent from the following description taken in conjunction with the drawings.

BRIEF DESCRIPTION OF DRAWINGS

The subject matter, which is regarded as the disclosure, is particularly pointed out and distinctly claimed in the claims at the conclusion of the specification. The foregoing and other features, and advantages of the disclosure are apparent from the following detailed description taken in conjunction with the accompanying drawings in which:

The detailed description explains embodiments of the disclosure, together with advantages and features, by way of example with reference to the drawings.

DETAILED DESCRIPTION

Embodiments of the present invention provide advantages in allowing the decontamination of an area containing a biological threat. Embodiments of the invention provide a decontamination device that includes a chemically stable decontamination material that may be selectively gasified to neutralize a biological threat. Embodiments of the invention provide a decontamination device that may be delivered to a remote location and activated to neutralize a biological threat. Embodiments of the invention further provide a decontamination device that may be delivered via an aerial vehicle.

Biological threats pose a hazard to humans and an area contaminated with such an organism needs to be neutralized before being suitable for occupation. As used herein the term "biological threat" refers to a biological organism that may be deployed to produce casualties in personnel or animals or damage plants. Examples of a biological threat include viruses and bacterial endospores, such as *Bacillus anthracis* (i.e. anthrax), *Bacillus subtilis* and Encephalomyelitis for example.

Figure 1:
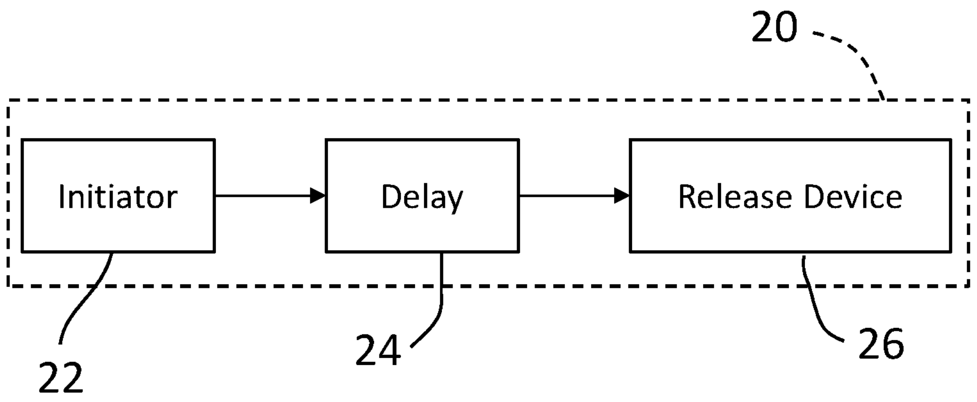
FIG. 1 is a block diagram of the decontamination system in accordance with an embodiment of the invention.
Figure 2:
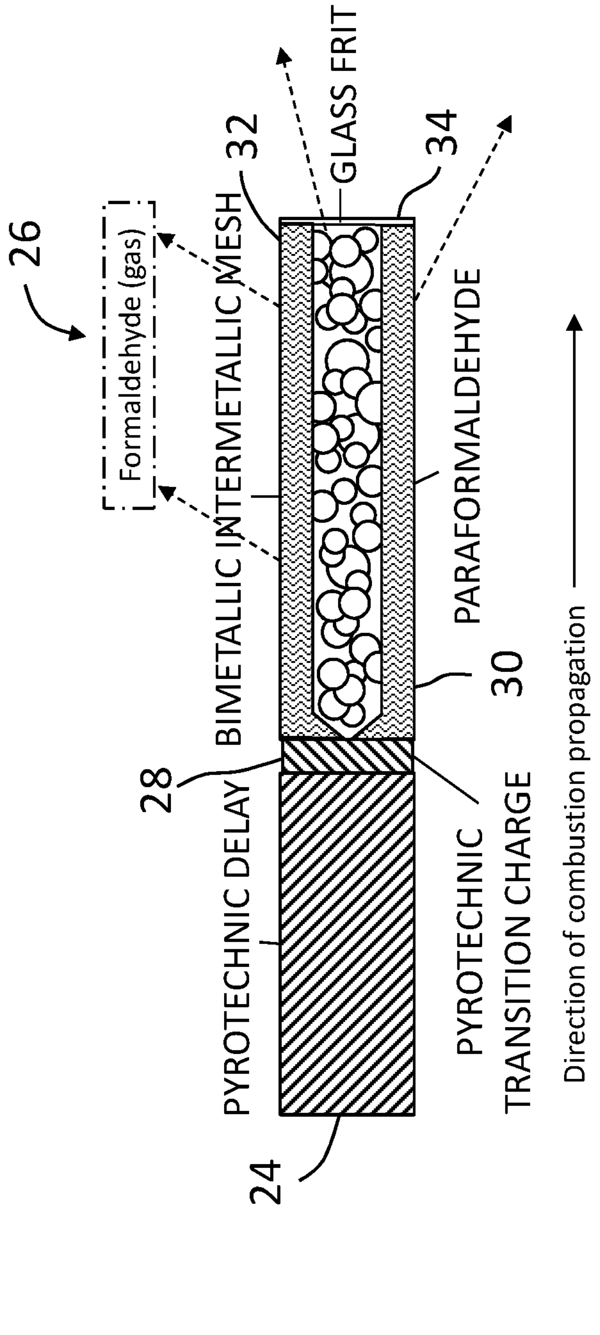
FIG. 2 is a partial sectional view of the decontamination system of FIG. 1 in accordance with an embodiment of the invention.

Referring now to FIG. 1 and FIG. 2, an embodiment is shown of a decontamination device 20. In one non-limiting embodiment. the decontamination device 20 includes an initiator 22 connected with a delay element 24. Coupled to the delay element 24 is a decontamination material release module 26. As will be discussed in more detail herein, the release module 26 converts a solid material into a gaseous decontamination agent in response to being thermally energized. The delay element 24 allows the initiation of the timing of the decontamination release after a predetermined amount of time following activation (e.g. burning) of the delay element 24 by the initiator 22. The initiator 22 may be any suitable type of device that provides for initiation of propagation or burning of the delay element 24. The initiator 22 may be an electrical, thermal, mechanical, optical or other device. In one embodiment, a transition charge 28 is disposed between the delay element 24 and the release module 26.

Referring now to FIG. 2, an embodiment of the decontamination device 20 is shown where the transition charge 28 is arranged between the delay element 24 and the release module 26. The delay element 24 may be any suitable delay device that is capable of repeatably and reliably activating in response to the initiator 22, waiting a predetermined amount of time and then activating the transition charge. In an embodiment, the amount of time delay may be between milliseconds to 10 seconds. In another embodiment, the amount of delay may be up to 30 seconds. The transition charge 28 is configured to provide sufficient thermal energy to activate a heating element 30. The transition charge 28 outputs the thermal energy in response to an input from the delay element 24. In one embodiment, the transition charge 28 is a material that has a reaction characterized by a large amount of heat (exothermic) with minimal gas generation, such as but not limited to a mixture of ferric oxide and metallic zirconium or a silicon with red lead oxide for example.

In one embodiment, the release module 26 includes the heating element 30. The heating element 30 is a heat source configured to transfer thermal energy to a paraformaldehyde material. The thermal energy transferred is sufficient to decompose the paraformaldehyde into formaldehyde gas. Paraformaldehyde has a melting point of about 248° F. (120° C.). Therefore, any heating source capable of transitioning the paraformaldehyde from a solid state to a formaldehyde gas may be used. It should be appreciated that while embodiments herein may describe a particular heating element that includes a self-alloying reaction to generate the thermal energy, this is for exemplary purposes and claimed invention should not be so limited. In other embodiments, the heating element 30 may be, but is not limited to: a resistance heater, a battery, a torch, a candle, a kerosene heater, a propane heater, a pyrotechnic device, a match (e.g. a combinations of red phosphorus and white phosphorus with a burnable material such as wood) and a steam generator for example.

In one non-limiting embodiment, the heating element 30 is generally cylindrical in shape and defines a generally hollow interior portion. In an embodiment, the heating element 30 is comprised of a bimetallic intermetallic mesh, such as that described in commonly owned U.S. Pat. Nos. 8,608,878 and 7,930,976, the contents of which are incorporated herein by reference. The structure of the heating element 30 may be comprised of a substrate comprised of a plurality of wires made from a first material and a coating made from a second material. The second material is chosen to be a reactive material that is different from that of the first material. The three-dimensional structure of the substrate is such that it has an appreciable amount of free volume (i.e., empty air space creating voids between crossing wires in the mesh substrate). The wires are preferably in intimate physical and, thus, thermal contact with one another at the intersections. In an exemplary preferred embodiment, the mesh substrate is commercially available from TWP, Inc. of Berkeley, Calif., and comprises a plurality of aluminum wires each with an approximate thickness or diameter in the range of from 0.0021 inches (200 wires per inch) to 0.0090 inches (40 wires per inch).

In an embodiment, the heating element 30 coating comprises nickel that is applied onto the outer surface of each of the wires of the aluminum metal mesh substrate by, for example, electroplating or other methods such as vacuum sputtering or through an electroless process. The nickel coating may include other materials including boron, phosphorus and/or palladium. Also, if aluminum is utilized as the mesh substrate material, any aluminum oxide that is present on the outer surface of the aluminum wires may be removed and a coating of zinc may be applied to the outer surface of the wires. The zinc may allow initiation or ignition of the structure at a lower temperature than if the zinc were not present. In the alternative, the zinc coating may be removed if an electroless process is used to coat the nickel onto the aluminum wire. The amount of nickel that is coated onto the aluminum mesh wires may be in a one to one ratio with the underlying aluminum wires; that is, the nickel may be in an equivalent molar content as that of the aluminum. The heat generating structure may be considered to be a reactive multilayer laminate comprising the substrate and the coating, with both the substrate and the coating comprising reactive metals.

The materials (e.g., metals) comprising the substrate and the coating are selected based on their individual characteristics, such as melting point and density, and in combination for enthalpy of alloying. For any bimetallic structure comprising a substrate of a first metal coated with a second, different metal to propagate, the formation of alloys from the individual metal constituent components must be exothermic. This heat evolved warms not only the surrounding environment, but also the continuous metal structure. After a source of ignition (e.g., transition charge 28) is applied to the heating element 30, the alloying temperature of at least one of the metals (typically that of the aluminum wire first) is eventually achieved and the materials are thermally energized and react with each other such that further alloying between the two metals is induced. Accordingly, heat is liberated with resulting propagation in a self-sustaining manner throughout the entire continuous heating element 30 from a first or starting point within the structure and along a travel path to a second or ending or discharge point within the structure, and in a controlled and manufacturable manner. The starting and ending points are typically spaced from each other with the travel path in between.

More specifically, the exothermic reaction between the dissimilar materials comprising the heating element can be made to occur at a relatively slower propagation or burn rate in part not only due to the composition of the dissimilar materials selected but also due to the three-dimensional characteristics of the substrate portion of the structure; in particular, to a non-uniform and varying distribution of the mass of the substrate and corresponding coating along the direction of the primary propagation or burn path. As will be discussed in more detail herein, the burn rate and the amount of thermal energy released by the heating element may be used to cause a phase change in a decontamination material allowing the decontamination material to change into a gaseous state and neutralize a biological threat.

In general, any material that can be prepared or formed as a foam substrate, a mesh substrate, or other non-completely-solid substrate may be used as the substrate. This includes various metals and non-metals. In an embodiment, the substrate material comprises aluminum and the coating comprises nickel coated that is either pure or combined with boron and/or phosphorus. The material comprising the substrate is typically selected in accordance with or in dependence on the material that will be coated onto the substrate. The material coated onto the substrate is preferably deposited in a reliable and consistent manner, for example by electrochemical means such as electroplating or by an autocatalytic electroless process. The materials that may comprise the substrate wires and/or the wire coating may include those from the group of reactive metals including aluminum, boron, carbon, silicon, zirconium, iron, copper, beryllium, tungsten, hafnium, antimony, magnesium, molybdenum, zinc, tin, nickel, palladium, phosphorus, sulfur, tantalum, manganese, cobalt, chromium, and vanadium.

Also, metal particles such as aluminum, magnesium, boron, beryllium, zirconium, titanium, zinc may be used in combination with fluoropolymers such as polytetrafluoroethylene, fluoroelastomers, fluorosurfactants, or fluoroadditives. As such, the metals may be formed in finely divided particles within a matrix of one of the polymers and extruded to form a wire-like structure such as a filament which is then integrated into the structure of the substrate. In the alternative, a tube made from aluminum for example, may be filled with the above noted metal particles mixed in with one of the above noted polymers. A plurality of such tubes may then be used to form the substrate. Additional materials that may be utilized include energetic polymers and plasticizers such as glycidyl azide polymer, polyoxetanes, or polyglycidyl nitrate. These materials may be used alone as the substrate material or in combination with any of the above reactive metals or non-reactive metals, for example, by forming these polymers and plasticizers around the metals in a wire-like structure which is then integrated into the structure of the substrate. Again, these energetic materials may be used either alone or in combination with any of the above reactive or non-reactive metals by placing them inside of an aluminum tube and having a plurality of such tubes comprise the substrate.

Further, the following non-energetic polymers can be combined with any of the above materials to form the substrate: hydroxyl terminated polybutadiene, hydroxyl terminated polyether, carboxy terminated polybutadiene, polyether, polycaprolactone, or polyvinyl chloride. Alternatively, such a combination of non-energetic polymers can be placed inside of an aluminum tube, where a plurality of such tubes comprises the substrate. In addition, there exist many powder-based reactions composed of a fuel and an oxidizer that constitute the bulk of pyrotechnic formulations. Incorporating these into the heating element 30 would include the use of a binder material, such as the energetic polymers and plasticizers listed above or the non-energetic polymers listed above, together with a non-reacting metal wire material.

Disposed within the interior of the heating element 30 is a solid decontamination element 32 made from a material suitable for neutralizing the biological threat being addressed. The decontamination element 32 is contained within the interior of heating element 30 by a glass frit 34 arranged on an end of the heating element 30 opposite the transition charge 28. In the exemplary embodiment, the decontamination element 32 is made from paraformaldehyde. Paraformaldehyde is a generally white crystalline solid having a density of about 1.42 g/$cm^3$ and a melting point of 120 C. Paraformaldehyde is the smallest polyoxymethylene, the polymerization product of formaldehyde with a typical degree of polymerization of 8-100 units. The paraformaldehyde may be depolymerized into formaldehyde gas by heating, such as by the thermal energy released during the exothermic and alloying reaction of heating element 30. The gasification of the paraformaldehyde into formaldehyde may then be released into the environment. It should be appreciated that since paraformaldehyde is a stable material at normal environmental temperatures, advantages are gained in ease of storage, transportation and handling of the decontamination device 20 prior to use. It has been found that biological threats, such as *Bacillis anthracis* (i.e. anthrax) for example, may be neutralized by fumigation with formaldehyde.

Figure 3:
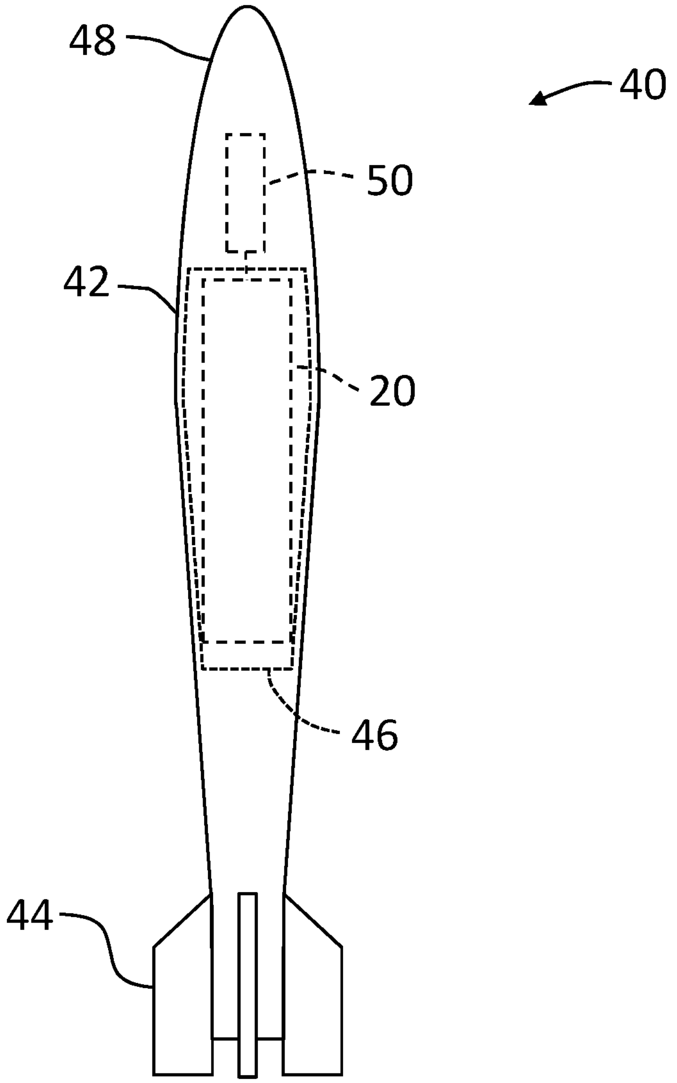
FIG. 3 is side view of a mortar shell for delivering the decontamination system in accordance with an embodiment of the invention.

When the decontamination device 20 is delivered to an area that has been contaminated by biological threats, that the initiator 22 may activate the delay element 24 and ultimately release formaldehyde gas through the gasification of paraformaldehyde. The formadehyde gas will neutralize the biological threat allowing human personnel to enter the area. It should further be appreciated that it is desirable to deliver the decontamination system 10 without requiring human operators to enter the contaminated area. Referring now to FIG. 3 one method is shown of remotely delivering a decontamination device 20 using a mortar shell 40.

The mortar shell 40 includes a shell body 42 carrying a conventional tail assembly 44 to which a conventional propulsion charge (not shown) is attached. The shell body 42 includes a central chamber 46 sized to receive the decontamination device 20. At the forward end 48 of the shell body 42 a fuse assembly, such as a firing pin 50 is arranged to activate the initiator 22. It should be appreciated that other types of activators may also be used to activate the initiator 22, in another embodiment a sensor such as an accelerometer may be used to transmit a signal to the initiator 22. The mortar shell 40 may include a power source, such as a battery for example, that facilitates activation of the initiator 22.

It should be appreciated that in other embodiments, the initiator 22 may activate prior to impact, such as on a timer for example. In still other embodiments, the initiator 22 may be activated at launch and the delay element 24 delays the activation of the release module 26 until the desired point in the trajectory of the mortar shell.

In operation, the deployment personnel configure the mortar tube (not shown) and propulsion charge to cause the mortar shell 40 to have a trajectory that places the shell in the contaminated area. The mortar shell 40 is fired from the mortar tube and lands in the contaminated area. At the predetermined point (e.g. impact), the initiator 22 activates causing the delay element 24 to burn. When the delay element 24 reaches the transition charge 28, the transition charge 28 activates and thermally energizes the heating element 30. The energizing of the heating element 30 results in an exothermic and self-sustaining alloying reaction. The heat from the exothermic reaction causes the paraformaldehyde material in the decontamination element 32 to change from a solid state to a gaseous state. It should be appreciated that upon impact, the gaseous formaldehyde will be released into the contaminated environment.

In one embodiment, the initiator 22 activates in response to the mortar shell 40 (or other delivery vehicle) striking a surface, such as a top of a barrel or drum for example. The delay element 24 is then configured to allow the mortar shell 40 to penetrate the contents of the drum before the formaldehyde gas is released.

It should be appreciated that while embodiments herein may make reference to a mortar shell as a vehicle for remotely delivering the decontamination system to the contamination area, this is for exemplary purposes and the claimed invention should not be so limited. In other embodiments, the delivery means may be another type of aerial vehicle, such as but not limited to an artillery shell, a rocket propelled grenade, a missile and an unmanned aerial vehicle. The vehicle may also be a ground or water based vehicle, such as a robot, an above water or an underwater unmanned vehicle for example. In still other embodiments, the decontamination device may be sized, shaped and configured to be thrown by personnel into the contaminated area. Further, in still other areas, the decontamination device may be placed by personnel in the contaminated area.

The term “about” is intended to include the degree of error associated with measurement of the particular quantity based upon the equipment available at the time of filing the application. For example, “about” can include a range of ±8% or 5%, or 2% of a given value.

The terminology used herein is for the purpose of describing particular embodiments only and is not intended to be limiting of the disclosure. As used herein, the singular forms “a”, “an” and “the” are intended to include the plural forms as well, unless the context clearly indicates otherwise. It will be further understood that the terms “comprises” and/or “comprising,” when used in this specification, specify the presence of stated features, integers, steps, operations, elements, and/or components, but do not preclude the presence or addition of one or more other features, integers, steps, operations, element components, and/or groups thereof.

While the disclosure is provided in detail in connection with only a limited number of embodiments, it should be readily understood that the disclosure is not limited to such disclosed embodiments. Rather, the disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that the exemplary embodiment(s) may include only some of the described exemplary aspects. Accordingly, the disclosure is not to be seen as limited by the foregoing description, but is only limited by the scope of the appended claims.

What is claimed is:

1. A method of decontaminating an area having biological organisms, the method comprising:

delivering a decontamination device to the area, the decontamination device having an igniter, a first element made from paraformaldehyde, and a second element;

thermally energizing the second element with the igniter;

forming an exothermic reaction in the second element in response to being thermally energized by the igniter;

transforming the paraformaldehyde into gaseous formaldehyde with the exothermic reaction; and neutralizing the biological organisms with the gaseous formaldehyde.

2. The method of claim 1, wherein the exothermic reaction of the second element is a self-sustaining alloying reaction.

3. The method of claim 2, wherein the exothermic reaction propagates from a first end of the second element to a second end of the second element.

4. The method of claim 3, wherein the propagation of the exothermic reaction occurs at a rate sufficient to convert the first element from a solid to a gas.

5. The method of claim 4, wherein the second element is generally cylindrical and is disposed about the first element.

6. The method of claim 1, wherein the decontamination device further includes a pyrotechnic delay element and a pyrotechnic charge between the igniter and the second element.

7. The method of claim 1, further comprising delivering the decontamination device via an aerial vehicle selected from a group consisting of a mortar shell, an artillery shell, a rocket propelled grenade, a missile and an unmanned aerial vehicle.

* * * * *